United States Patent
Bae et al.

(10) Patent No.: US 9,867,570 B2
(45) Date of Patent: Jan. 16, 2018

(54) APPARATUS FOR DETERMINING EXERCISE CAPABILITY OF USER AND OPERATING METHOD THEREOF

(71) Applicants: Samsung Electronics Co., Ltd., Suwon-si (KR); University-Industry Cooperation Group of Kyung Hee University, Yongin-si (KR)

(72) Inventors: Sang Kon Bae, Seongnam-si (KR); Byung Hoon Ko, Hwaseong-si (KR); Choong Hee Lee, Seoul (KR); Sub Sunoo, Yongin-si (KR); Sang-Seok Nam, Suwon-si (KR); Hun-Young Park, Incheon (KR)

(73) Assignees: Samsung Electronics Co., Ltd., Suwon-si (KR); UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 108 days.

(21) Appl. No.: 14/692,207

(22) Filed: Apr. 21, 2015

(65) Prior Publication Data
US 2016/0113575 A1 Apr. 28, 2016

(30) Foreign Application Priority Data
Oct. 24, 2014 (KR) .................. 10-2014-0145493

(51) Int. Cl.
A61B 5/02 (2006.01)
A61B 5/00 (2006.01)
A61B 5/024 (2006.01)
A61B 5/22 (2006.01)

(52) U.S. Cl.
CPC ............ *A61B 5/4884* (2013.01); *A61B 5/024* (2013.01); *A61B 5/222* (2013.01); *A61B 5/7275* (2013.01)

(58) Field of Classification Search
CPC ....... A61B 5/4884; A61B 5/024; A61B 5/222; A61B 5/7275
See application file for complete search history.

(56) References Cited

U.S. PATENT DOCUMENTS

| | | | |
|---|---|---|---|
| 6,361,501 B1 * | 3/2002 | Amano | A61B 5/02028 600/485 |
| 2002/0156386 A1 * | 10/2002 | Dardik | A61B 5/0002 600/520 |
| 2013/0231576 A1 * | 9/2013 | Tanaka | A61B 5/0205 600/484 |

* cited by examiner

*Primary Examiner* — Lindsey G Wehrheim
(74) *Attorney, Agent, or Firm* — NSIP Law

(57) ABSTRACT

An apparatus determining an exercise capability of an individual by obtaining heart rate information of the individual, detecting a characteristic point from the heart rate information, and obtaining information to be used to determine the exercise capability of the individual based on the characteristic point.

19 Claims, 9 Drawing Sheets

APPARATUS FOR DETERMINING EXERCISE CAPABILITY OF USER AND OPERATING METHOD THEREOF

CROSS-REFERENCE TO RELATED APPLICATION(S)

This application claims the benefit under 35 USC 119(a) of Korean Patent Application No. 10-2014-0145493, filed on Oct. 24, 2014, in the Korean Intellectual Property Office, the entire disclosure of which is incorporated herein by reference for all purposes.

BACKGROUND

1. Field

The following description relates to an apparatus for determining an exercise capability of an individual, and an operating method thereof.

2. Description of Related Art

By analyzing respiration or a change in a blood lactate density of a user exercising on a treadmill or an ergometer, a point in time at which a biometric signal of the user changes is detected. Through the detection, an exercise capability of the user is evaluated.

As described above, equipment, for example, a treadmill or an ergometer are used to evaluate an exercise capability of a user, and separate equipment is used to analyze respiration or a blood lactate density. Additionally, to evaluate the exercise capability of the user, the user exercises until the user is exhausted.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an apparatus capable of determining an exercise capability of an individual, the apparatus including an obtainer configured to obtain heart rate information of an individual, a detector configured to detect a characteristic point from the obtained heart rate information, and a determiner configured to obtain determination information to be used to determine the exercise capability of the individual based on the characteristic point.

The apparatus may further include an output unit configured to output at least one of a visual indicating information, an auditory indicating information, and a tactile indicating information to the individual using a preset scheme.

The output unit may be configured to suspend an output of at least one of the visual indicating information, the auditory indicating information, and the tactile indicating information when the characteristic point is detected.

The determiner may be further configured to obtain additional heart rate information corresponding to anaerobic threshold information of the individual based on at least one of the characteristic point and physical information of the user.

The determiner may be further configured to determine the exercise capability based on the additional heart rate information corresponding to the anaerobic threshold information.

The detector may be configured to detect the characteristic point based on a change in the heart rate information with respect to an exercise tolerance of the individual.

The apparatus may further include an exercise guider configured to provide exercise guidance information based on the exercise capability when the exercise capability is determined based on the determination information.

The apparatus may include a wearable device.

In another general aspect, there is also provided a method of determining an exercise capability of an individual, the method including obtaining heart rate information of the individual, detecting a characteristic point from the obtained heart rate information, and obtaining determination information to be used to determine an exercise capability of the individual based on the characteristic point.

The method may further include outputting at least one of a visual indicating information, an auditory indicating information, and a tactile indicating information to the individual using a preset scheme.

The outputting may further include suspending an output of at least one of the visual indicating information, the auditory indicating information, and the tactile indicating information when the characteristic point is detected.

The determining of the exercise capability may include obtaining additional heart rate information corresponding to anaerobic threshold information of the individual based on at least one of the characteristic point and physical information of the individual.

The determining of the exercise capability may further include determining the exercise capability based on the additional heart rate information corresponding to the anaerobic threshold information.

The detecting may include detecting the characteristic point based on a change in the heart rate information with respect to an exercise tolerance of the individual.

The method may further include providing exercise guidance information based on the exercise capability when the exercise capability is determined based on the determination information.

The apparatus may include a wearable device.

The method may further include detecting the characteristic point using a predetermined scheme.

In another general aspect, there is provided an apparatus capable of determining an exercise capability of an individual, the apparatus including a heart rate sensor configured to obtain first heart rate information of the individual; a detector configured to detect a characteristic point from the obtained first heart rate information; and a determiner configured to obtain determination information to be used to determine the exercise capability of the individual based on the characteristic point and second heart rate information.

Other features and aspects will be apparent from the following detailed description, the drawings, and the claims.

Figure 1:
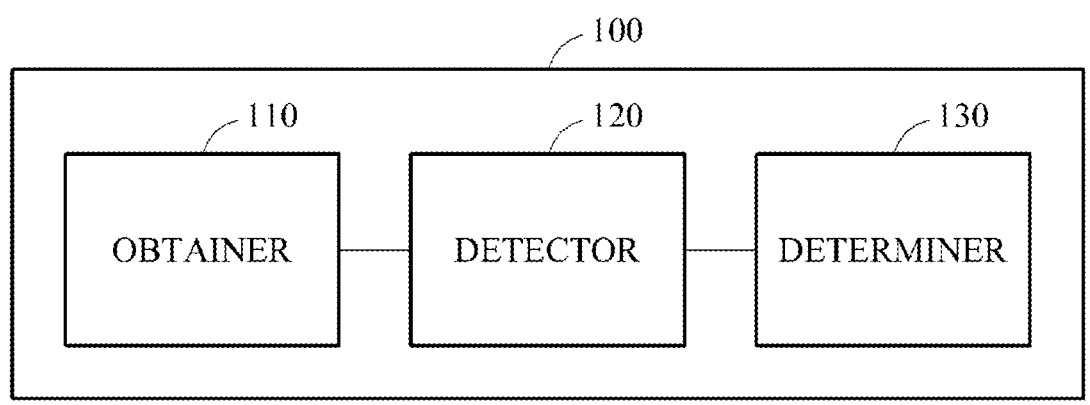
FIG. 1 is a block diagram illustrating an example of an apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, reference will now be made in detail to examples with reference to the accompanying drawings, wherein like reference numerals refer to like elements throughout. Various alterations and modifications may be made to the examples. Here, the examples are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "include/comprise" and/or "have" when used in this specification, specify the presence of stated features, integers, steps, operations, elements, components, and/or combinations thereof, but do not preclude the presence or addition of one or more other features, numbers, steps, operations, elements, components, and/or groups thereof.

Unless otherwise defined, all terms including technical and scientific terms used herein have the same meaning as commonly understood by one of ordinary skill in the art to which examples belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the examples with reference to the accompanying drawings, like reference numerals refer to like constituent elements and a repeated description related thereto will be omitted. When it is determined detailed description related to a related known function or configuration they may make the purpose of the examples unnecessarily ambiguous in describing the examples, the detailed description will be omitted here.

FIG. 1 is a block diagram illustrating an example of an apparatus.

Referring to FIG. 1, the apparatus 100 includes an output unit (not shown), an obtainer 110, a monitoring unit (not shown), a detector 120, and a determiner 130. An individual exercises while wearing the apparatus 100 on his or her body.

The output unit outputs auditory indicating information to the individual using a preset scheme. For example, when the individual wears the apparatus 100 on a wrist and starts to exercise, the output unit may output 54 beeps to the individual for one minute after the individual starts to exercise. After one minute, the output unit may output 72 beeps to the individual for a subsequent one minute. The apparatus 100 sets a scheme of outputting the auditory indicating information to progressively increase an exercise tolerance of the individual. The individual may increase an intensity of the exercise through the beeps.

Further, the output unit outputs at least one of a tactile indicating information and a visual indicating information to the individual. For example, the output unit drives an oscillation motor to output an oscillation using a preset scheme. In addition, the output unit outputs a light using a preset scheme.

The output unit continuously outputs at least one of the visual indicating information, the auditory indicating information, and the tactile indicating information to the individual until the individual terminates the exercise. When a characteristic point is detected from heart rate information of the individual, the apparatus 100 provides the individual with a message requesting suspension of the exercise, and the output unit suspends an output of the visual indicating information, the auditory indicating information, and the tactile indicating information.

The obtainer 110 obtains heart rate information of the individual. For example, the obtainer 110 obtains the heart rate information of the individual using a heart rate sensor such as, a photoplethysmogram (PPG) sensor.

The monitoring unit monitors a change in the heart rate information of the individual. The monitoring unit preprocess the obtained heart rate information before monitoring the change in the heart rate information. The heart rate information of the individual may change continuously over time. Thus, the monitoring unit preprocess the obtained heart rate information to readily monitor the change in the heart rate information. For example, the monitoring unit performs a moving average on the obtained heart rate information.

Since the individual is exercising while wearing the apparatus 100, the apparatus 100 may move. Thus, the monitoring unit removes motion noise through preprocessing. The monitoring unit monitors the change in the heart rate information based on the preprocessed heart rate information.

The detector 120 detects a characteristic point from the obtained heart rate information using a predetermined scheme. When the individual adjusts the intensity of the exercise to correspond to the auditory indicating information output from the apparatus 100, the exercise tolerance of the individual progressively increases. The detector 120 detects the characteristic point based on the change in the heart rate information with respect to the exercise tolerance of the individual. While the exercise tolerance of the individual progressively increases, the heart rate information of the individual also increases. The change in the heart rate information of the individual may be substantially uniform. The heart rate information of the individual may progressively increase, and then sharply increase at the characteristic point. The detector 120 detects the characteristic point at which the heart rate information of the individual sharply increases.

For example, the detector 120 differentiates the obtained heart rate information. A gradient of the heart rate information may change at the characteristic point. When the heart rate information is primarily differentiated, the primary differentiation may have a peak at the characteristic point. When the heart rate information is secondarily differentiated, the secondary differentiation at the characteristic point may be zero. The detector 120 determines a point corresponding to a peak value obtained through the primary differentiation to be the characteristic point. Also, the detector 120 determines a point corresponding to a zero value obtained through the secondary differentiation to be the characteristic point.

In another example, the detector 120 detects the characteristic point based on a change between the heart rate information and heart rate information obtained adjacent to the heart rate information. The detector 120 verifies changes among heart rate information obtained at, for example, a first point, a second point and a third point. For example, the first point may correspond to a point in time at which one minute passes after the individual starts to exercise. The second point may correspond to a point in time at which one minute and thirty seconds pass, after the individual begins to exercise. The third point may correspond to a point in time at which two minutes pass after the individual begins to exercise. When the change in the heart rate information between the first point and the second point is identical to or substantially identical to the change in the heart rate information between the second point and the third point, the detector 120 determines that no characteristic point exists at the first point, the second point, and the third point. When the change in the heart rate information between the second point and the third point is greater than the change in the heart rate information between the first point and the second point, the detector 120 estimates that a characteristic point exists at the second point. It is noted that this is only an example and the characteristic point may be determined differently. For example if the change in the heart rate information between the second point and the third point is less than the change in the heart rate information between the first point and the second point, the detector 120 may also estimate that a characteristic point exists at the second point. Similarly, the use of three points to estimate the characteristic point is simply an example and more than three points may be used to estimate the characteristic point.

In still another example, the detector 120 detects the characteristic point using a preset threshold value. The heart rate information of the individual is stored in the apparatus 100 and/or a server communicating with the apparatus 100. The apparatus 100 detects a point at which a change in the heart rate information or a gradient of the heart rate information increases based on the stored heart rate information. The apparatus 100 sets a change value corresponding to the detected point as the threshold value. When the change in the heart rate information of the individual performing the exercise reaches a vicinity of the threshold value or exceeds the threshold value, the apparatus 100 determines a point at which the change in the heart rate information reaches the vicinity of the threshold value or a point at which the change in the heart rate information exceeds the threshold value to be the characteristic point.

The detector 120 obtains heart rate information at the characteristic point through detection of the characteristic point.

The foregoing methods of detecting the characteristic point are provided as examples only. Accordingly, a method of detecting a characteristic point is not limited thereto.

The determiner 130 obtains determination information to be used to determine the exercise capability of the individual based on the detected characteristic point. The determiner 130 obtains heart rate information corresponding to anaerobic threshold information of the individual based on at least one of the heart rate information at the characteristic point and physical information of the individual. For example, when the heart rate information at the characteristic point corresponds to "130", the determiner 130 obtains first heart rate information corresponding to the characteristic point based on the heart rate information of "130", an age, a height, and a weight of the individual. The determiner 130 obtains second heart rate information corresponding to ventilatory threshold (VT) information of the individual from the first heart rate information using a predefined relationship. The determiner 130 determines the exercise capability indicating whether the individual is capable of performing an exercise at a relatively high intensity or at a relatively low intensity, based on the second heart rate information. The apparatus 100 transmits the first heart rate information to a server or another apparatus connected to the apparatus 100, and receives the second heart rate information from the server or the other apparatus. The apparatus 100 determines the exercise capability of the individual based on the received second heart rate information.

In another example, the determiner 130 obtains information on a time used until the characteristic point is detected, and determines the exercise capability of the user based on the time information. When a relatively long time is used to detect the characteristic point, the determiner 130 determines that the individual is capable of performing an exercise at a relatively high intensity. When a relatively short time is used to detect the characteristic point, the determiner 130 determines that the individual is incapable of performing an exercise at a relatively high intensity.

The apparatus 100 may further include an exercise guider (not shown) configured to provide exercise guidance information based on the exercise capability. The apparatus 100 generates exercise guidance information suitable for the exercise capability of the user. The apparatus 100 transmits the exercise capability to the other apparatus and/or the server through a communication interface. The other apparatus and/or the server generates exercise guidance information suitable for the exercise capability, and transmits the generated exercise guidance information to the apparatus 100. The exercise guider provides the individual with at least one of the exercise guidance information generated by the apparatus 100 and the exercise guidance information received by the apparatus 100.

The communication interface of the apparatus 100 includes wireless Internet interfaces such as a wireless local area network (WAN), a wireless fidelity (Wi-Fi) direct, a digital living network alliance (DLNA), a wireless broadband (WiBro), a world interoperability for microwave access (WiMAX), and a high speed downlink packet access (HSDPA), for example, and short-range communication interfaces such as Bluetooth, a radio frequency identification (RFID), an infrared data association (IrDA), a ultra wideband (UWB), ZigBee, and a near field communication (NFC). The communication interface also includes all interfaces that may communicate with an external device, for example, wired interfaces.

The apparatus 100 may further include a display (not shown). For example, the display may be a flexible display. The apparatus 100 displays the obtained heart rate information on the display. The apparatus 100 outputs a message to request an increase in an exercise speed through the display so that the exercise tolerance of the individual increases. The individual increases the exercise speed in response to the message. When the characteristic point is detected, the apparatus 100 displays, on the display, the heart rate information at the characteristic point, and the time used to detect the characteristic point. The apparatus 100 determines the exercise capability of the individual based on the characteristic point, and displays, on the display, an optimal intensity of an exercise that the individual is capable of performing. The apparatus 100 displays, on the display, the exercise guidance information suitable for the determined exercise capability. When the individual exercises while wearing the apparatus 100, the apparatus 100 coaches the individual for an exercise based on the exercise guidance information.

For example, the individual verifies his or her exercise capability through the apparatus 100, without using an exercise tolerance device such as a treadmill or an ergometer. To verify the exercise capability of the individual, the individual performs an exercise until a characteristic point is detected, rather than performing an exercise until the individual is exhausted. Accordingly, the individual does not need to wear a mask for a respiratory gas analysis to verify his or her exercise capability. Similarly, the individual does not need to use a blood test device for a blood lactate density analysis to verify his or her exercise capability.

Figure 2:
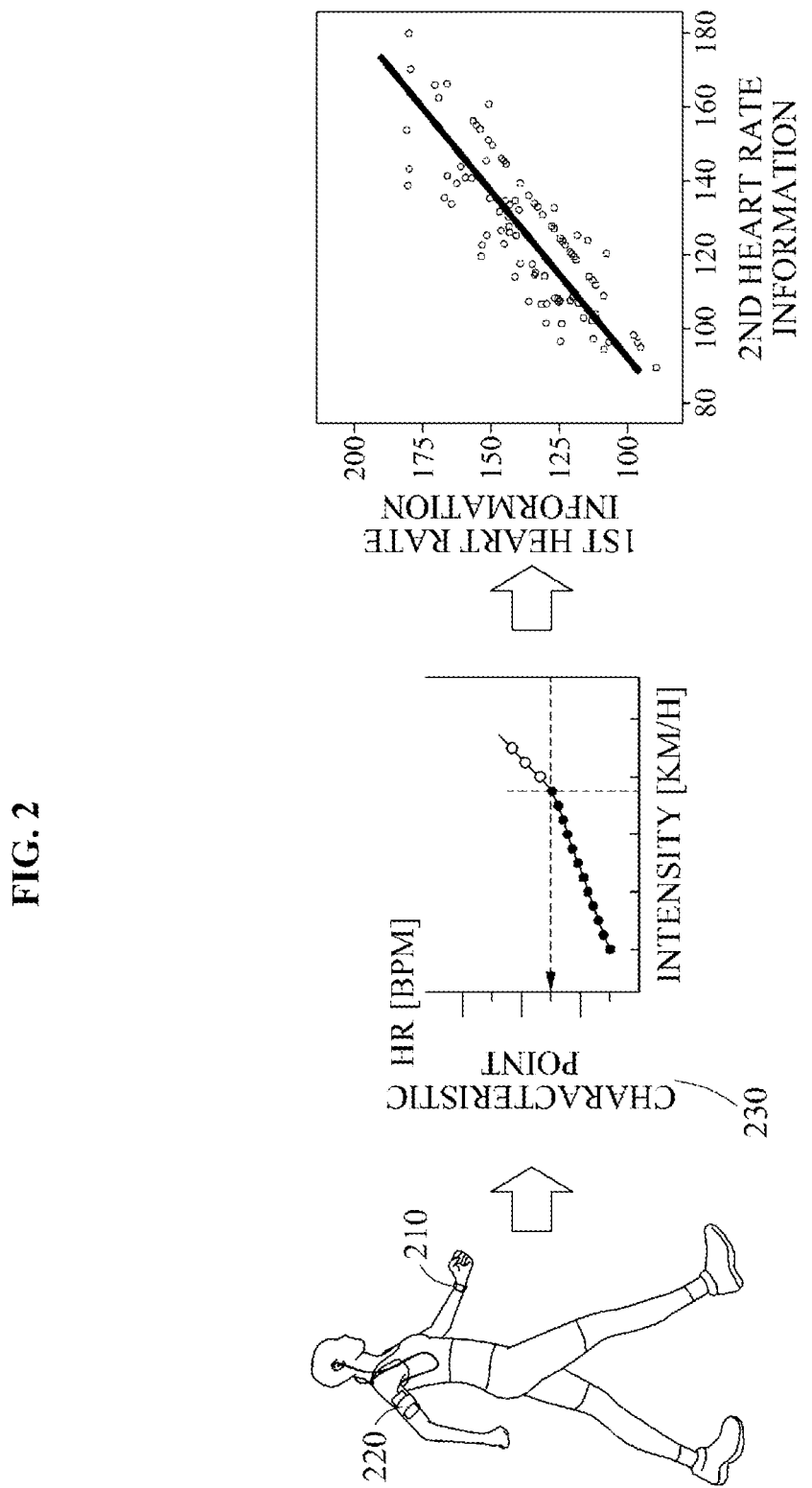
FIG. 2 illustrates an example of evaluating an exercise capability through an apparatus.

FIG. 2 illustrates an example of evaluating an exercise capability through an apparatus. The apparatus includes a wearable device or a mobile apparatus.

An individual wears a wearable device 210 on a wrist, and performs an exercise while carrying a mobile apparatus 220. In this example, the mobile apparatus 220 is connected to an earphone through an output apparatus, and provides auditory indicating information to the individual through the earphone. The individual performs an exercise capability measurement application stored in the wearable device 210 and/or the mobile apparatus 220. When the individual initiates an exercise, the wearable device 210 requests the mobile apparatus 220 paired with the wearable device 210 to output auditory indicating information. The wearable device 210 outputs an auditory indicating information to the individual.

The individual adjusts an exercise tolerance of the individual to correspond to the auditory indicating information. The auditory indicating information is output using a preset scheme. For example, 54 beeps may be output for one minute after a point in time at which the exercise is initiated, and 72 beeps may be output for the next one minute. When two minutes pass after the point in time at which the exercise is initiated, 90 beeps may be output for two minutes.

The wearable device 210 obtains heart rate information of the individual. Since the individual is exercising, the heart rate information of the individual increases. The wearable device 210 transmits the heart rate information to the paired mobile apparatus 220. The wearable device 210 and/or the mobile apparatus 220 monitor a change in the heart rate information. Based on a result of the monitoring, the wearable device 210 and/or the mobile apparatus 220 detect a point at which the heart rate information suddenly changes.

The wearable device 210 and/or the mobile apparatus 220 detect, from the heart rate information of the individual, a characteristic point 230 corresponding to a point at which a gradient of the heart rate information changes.

The wearable device 210 and/or the mobile apparatus 220 obtain first heart rate information corresponding to the characteristic point 230 based on the heart rate information at the characteristic point 230, a height, a weight, and an age of the individual. However, it is noted that the characteristic point 230, the height, the weight, and the age of the individual are examples for obtaining the first heart rate information and therefore more or less features may be used to obtain the first heart rate information. The wearable device 210 and/or the mobile apparatus 220 obtain second heart rate information corresponding to anaerobic threshold information of the user from the first heart rate information using a predefined relationship.

For example, the anaerobic threshold information corresponds to VT information. When the individual performs a progressive tolerance exercise, a ventilatory volume of the individual uniformly increases in a range of 50 to 75% of a maximum oxygen uptake of the individual. The ventilatory volume of the individual uniformly increases and then, sharply increases at a point. The point indicates the VT information of the individual. The wearable device 210 and/or the mobile apparatus 220 obtain the second heart rate information corresponding to the point at which the ventilatory volume of the individual sharply increases, based on the first heart rate information.

The wearable device 210 and/or the mobile apparatus 220 obtain heart rate information substantially identical to heart rate information analyzed after the individual performs an exercise until he or she is exhausted, without having to perform the exercise until the individual is exhausted.

The wearable device 210 and/or the mobile apparatus 220 determine the exercise capability of the individual based on the second heart rate information. The wearable device 210 and/or the mobile apparatus 220 verify whether the individual is capable of performing an exercise at a relatively high intensity or at a relatively low intensity.

FIGS. 3A through 3C and FIG. 4 illustrate examples of detecting a characteristic point.

Figure 3A:
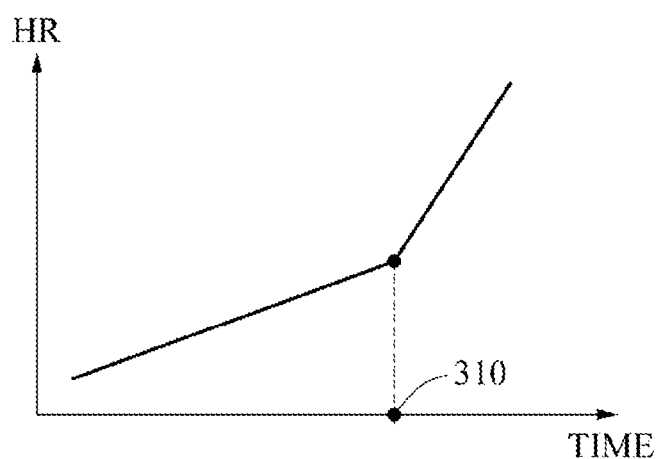
FIGS. 3A through 3C and FIG. 4 illustrate examples of detecting a characteristic point.
Figure 3B:
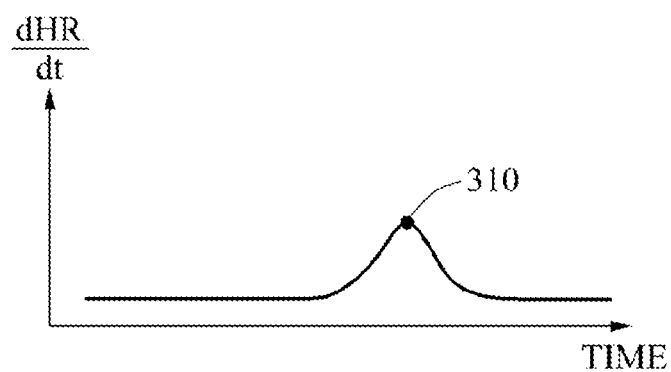
Figure 3C:
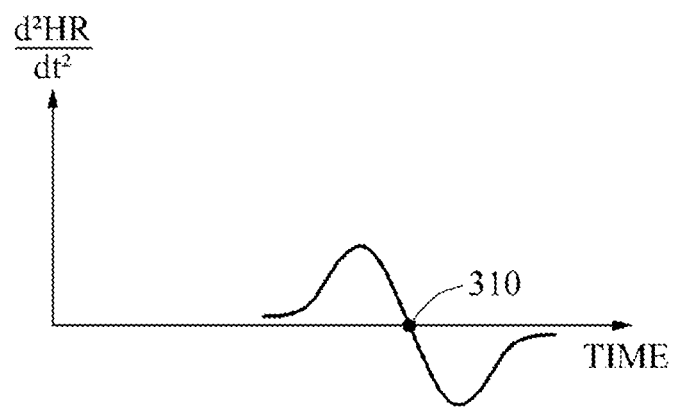

Referring to FIGS. 3A through 3C, a characteristic point is detected by differentiating heart rate information. When an individual performs an exercise, an apparatus obtains heart rate information as shown in FIG. 3A. At a characteristic point 310, a heart rate of the individual sharply increases.

The apparatus primarily differentiates the heart rate information, and a result of the primary differentiation is shown in FIG. 3B. At the characteristic point 310, the result of the primary differentiation has a peak value. The apparatus identifies a point in time at which the result of the primary differentiation starts to decrease, and detects the peak value of the primary differentiation through the identification.

The apparatus secondarily differentiates the heart rate information. A result of the secondary differentiation is shown in FIG. 3C. At the characteristic point 310, the result of the secondary differentiation corresponds to zero. The apparatus identifies a point at which the result of the secondary differentiation corresponds to a negative number, and verifies a point at which the result of the secondary differentiation corresponds to zero through the identification.

The apparatus determines the point at which the result of the primary differentiation has a peak, or the point at which the result of the secondary differentiation corresponds to zero to be the characteristic point. The apparatus monitors the result of the primary differentiation, and identifies the point at which the result of the primary differentiation decreases as a result of the monitoring. The apparatus detects the characteristic point through the identification. The apparatus monitors the result of the secondary differentiation, and identifies the point at which the result of the secondary differentiation corresponds to a negative number as a result of the monitoring. The apparatus detects the characteristic point through the identification. When the characteristic point is detected, the apparatus outputs a message to request suspension of the exercise to the individual, and suspends an output of indicating information having been continuously output while the individual is exercising.

The descriptions of FIGS. 3A though 3C are provided as examples only and the detection of the characteristic point is not limited thereto.

Figure 4:
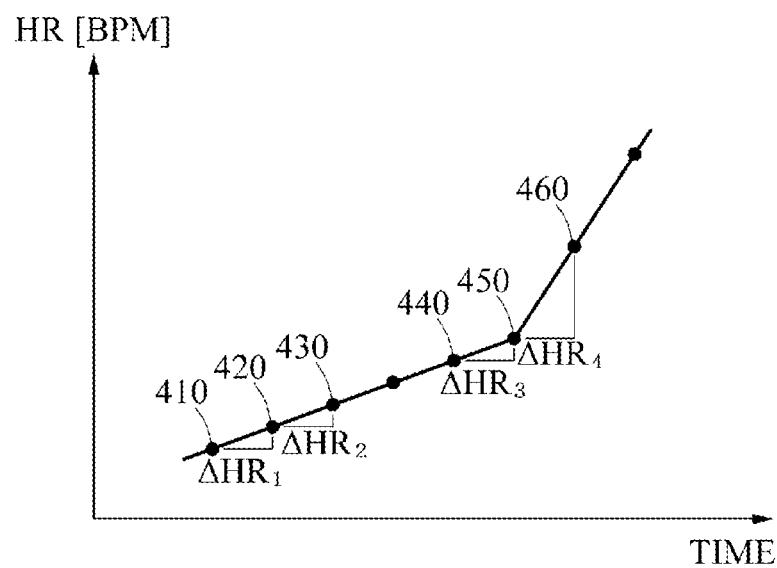

Referring to FIG. 4, heart rate information of an individual obtained by an apparatus is illustrated.

Each of heart rate information 410 through heart rate information 460 may be a mean value of heart rate information obtained for a predetermined time period, for example, one minute. For example, the heart rate information 410 may be an average of heart rate information obtained for one minute after a point in time at which an exercise is initiated, and the heart rate information 420 through the heart rate information 460 may be values obtained based on a moving average.

A difference $\Delta HR_1$ between the heart rate information 420 and the heart rate information 410 may be substantially identical to a difference $\Delta HR_2$ between the heart rate information 430 and the heart rate information 420. A difference $\Delta HR_3$ between the heart rate information 450 and the heart rate information 440 may differ from a difference $\Delta HR_4$ between the heart rate information 460 and the heart rate information 450. When the difference $\Delta HR_4$ between the heart rate information 460 and the heart rate information 450 is greater than the difference $\Delta HR_3$ between the heart rate information 450 and the heart rate information 440, the apparatus verifies that the heart rate information of the individual greatly changes between the heart rate information 450 and the heart rate information 460. The apparatus determines the heart rate information 450 to be a characteristic point based on the verification. The apparatus determines heart rate information of the individual between the heart rate information 450 and the heart rate information 460 to be the characteristic point based on the verification.

When the characteristic point is determined, the apparatus outputs a message to request suspension of the exercise to the individual.

The descriptions of FIG. 4 are provided as examples only and the detection of the characteristic point is not limited thereto.

Figure 5:
FIGS. 5 through 7 illustrate examples of a progressive exercise tolerance.
Figure 6:
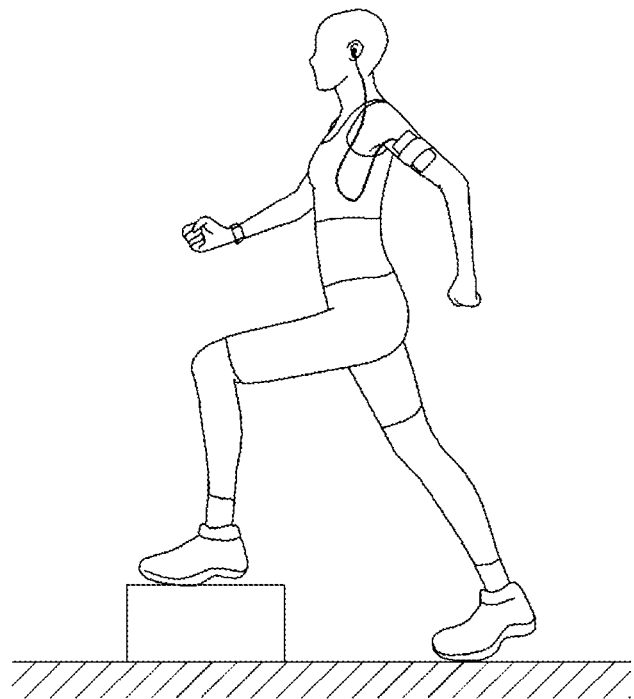
Figure 7:
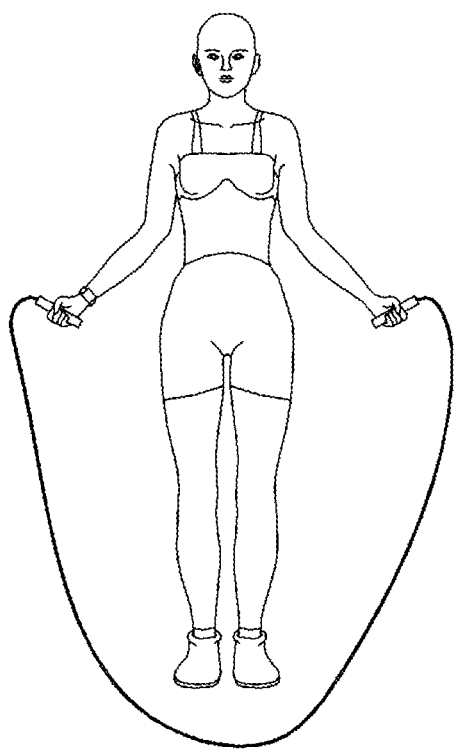

FIGS. 5 through 7 illustrate examples of a progressive exercise tolerance.

A individual may verify his/her exercise capability by performing exercises as shown in FIGS. 5 through 7, without using an exercise tolerance device such as a treadmill, for example.

Referring to FIG. 5, a shuttle run is illustrated. The shuttle run refers to an exercise of running back and forth over a predetermined distance.

An individual wearing an apparatus runs a predetermined distance back and forth. In this example, the apparatus outputs a beep to the individual using a preset scheme. The apparatus sets a scheme of outputting a beep to progressively increase an exercise tolerance of the individual.

When the individual performs shuttle run, heart rate information of the individual increases. The apparatus detects a point at which the heart rate information of the individual sharply increases. When the point is detected, the apparatus outputs a message indicating a request for suspension of the shuttle run to the individual. For example, the apparatus provides an oscillation to the individual, and provides a beep to the individual to request a termination of the exercise.

The apparatus determines the exercise capability of the individual based on the point.

Referring to FIG. 6, a step exercise is illustrated. The step exercise refers to a motion of an individual stepping up and down on a step.

The individual performs the step exercise to a beep output through an apparatus. The apparatus increases an output speed of the beep, and an exercise tolerance of the individual performing the step exercise to the output beep progressively increases. With the increase in the exercise tolerance, heart rate information of the individual increases and then, sharply increases at a predetermined point in time. The apparatus detects a point at which the heart rate information sharply increases. When the point is detected, the apparatus outputs a massage indicating a request for suspension of the step exercise to the individual.

Referring to FIG. 7, a jump rope is illustrated.

An individual wears an apparatus, and performs a jump rope. The individual performs the jump rope to an oscillation output from the apparatus. The apparatus monitors heart rate information of the individual, and detects a point at which the heart rate information suddenly changes based on a result of the monitoring.

The exercises illustrated in FIGS. 5 through 7 are provided as examples only, and the progressive exercise tolerance is not limited to the descriptions of FIGS. 5 through 7.

Figure 8:
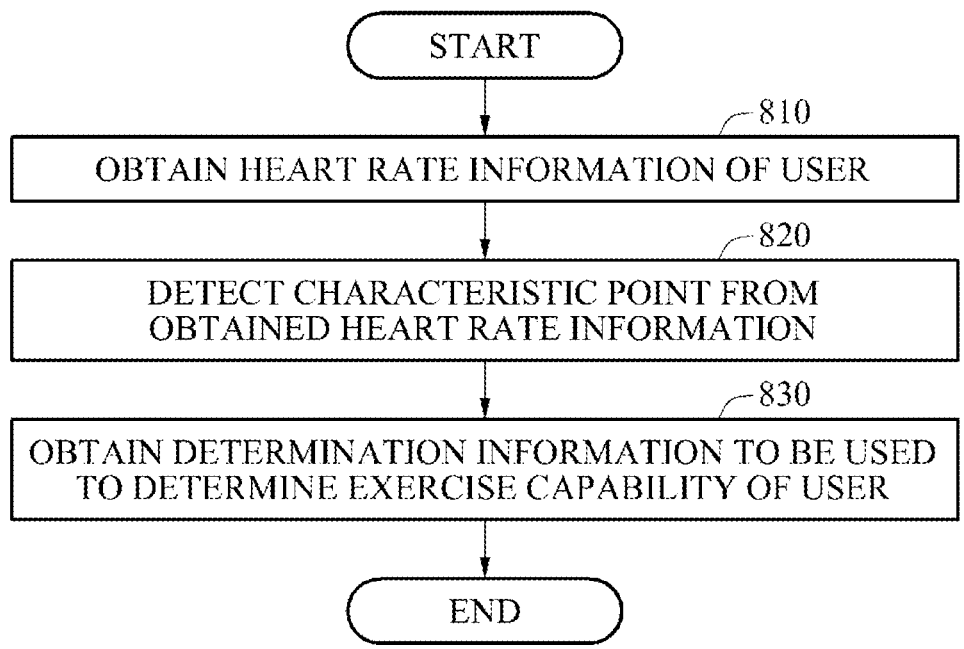
FIG. 8 is a flowchart illustrating an example of a method of evaluating an exercise capability using an apparatus.

FIG. 8 is a flowchart illustrating an example of a method of evaluating an exercise capability using an apparatus. The apparatus includes at least one of a wearable device and a mobile apparatus.

Referring to FIG. 8, in operation 810, the apparatus obtains heart rate information of an individual. The apparatus obtains the heart rate information using a heart rate sensor.

In operation 820, the apparatus detects a characteristic point from the obtained heart rate information using a predetermined scheme. For example, the individual detects the characteristic point based on a change in the heart rate information with respect to an exercise tolerance of the individual. The apparatus detects a point at which the heart rate information suddenly changes as the characteristic point, and obtains heart rate information at the characteristic point.

In operation 830, the apparatus obtains determination information to be used to determine an exercise capability of the individual based on the characteristic point. For example, the apparatus obtains additional heart rate information corresponding to anaerobic threshold information of the individual based on at least one of the characteristic point and physical information of the individual. The apparatus obtains the additional heart rate information corresponding to VT information of the individual based on the heart rate information at the characteristic point, a height, a weight, and an age of the individual but is not limited thereto. For example, the additional heart rate information may be obtained using more or less of the elements discussed above.

The apparatus determines the exercise capability of the individual based on the additional heart rate information corresponding to the VT information.

Further, the apparatus outputs at least one of a visual indicating information, an auditory indicating information, and a tactile indicating information to the individual using a preset scheme. When the characteristic point is detected, the apparatus suspends an output of at least one of the visual indicating information, the auditory indicating information, and the tactile indicating information.

When the exercise capability of the individual is determined based on the determination information, the apparatus provides exercise guidance information based on the exercise capability. For example, the apparatus provides the exercise guidance information based on the exercise capability by referring to a predefined table. The apparatus transmits the exercise capability to a server, and the server generates exercise guidance information based on the received exercise capability. The apparatus receives the exercise guidance information from the server, and provides the received exercise guidance information.

The descriptions provided with reference to FIGS. 1 through 7 may be applicable to the descriptions provided with reference to FIG. 8 and thus, duplicated descriptions will be omitted for conciseness.

The methods described herein may be recorded in non-transitory computer-readable media including program instructions to implement various operations embodied by a computer. The media may also include, alone or in combination with the program instructions, data files, data structures, and the like. The program instructions recorded on the media may be those specially designed and constructed for the purposes embodied herein, or they may be of the kind well-known and available to those having skill in the computer software arts. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

The various modules, elements, and methods described above may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Functional programs, codes, and code segments for implementing the examples disclosed herein can be easily constructed by a programmer skilled in the art to which the examples pertain based on the drawings and their corresponding descriptions as provided herein.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for determining an exercise capability of an individual, the apparatus comprising:
    an obtainer configured to obtain heart rate information of the individual while the individual performs an exercise;
    a detector configured to detect a characteristic point from the obtained heart rate information,
    wherein the characteristic point corresponds to a point at which a gradient of the heart rate information changes;
    a determiner configured to
        determine an elapsed time until the characteristic point is detected, and
        obtain determination information to be used to determine the exercise capability of the individual based on the characteristic point and the elapsed time; and
    an exercise guider configured to provide exercise guidance information based on the determined exercise capability.

2. The apparatus of claim 1, further comprising:
    an output unit configured to output information comprising at least one of a visual indicating information, an auditory indicating information, or a tactile indicating information to the individual using a preset scheme.

3. The apparatus of claim 2, wherein the output unit is further configured to suspend an output of at least one of the visual indicating information, the auditory indicating information, and the tactile indicating information when the characteristic point is detected.

4. The apparatus of claim 2, wherein the information instructs the individual to increase an intensity of the exercise until the characteristic point is detected.

5. The apparatus of claim 1, wherein the determiner is further configured to obtain additional heart rate information corresponding to anaerobic threshold information of the individual based on at least one of the characteristic point and physical information of the individual.

6. The apparatus of claim 5, wherein the determiner is further configured to determine the exercise capability based on the additional heart rate information corresponding to the anaerobic threshold information.

7. The apparatus of claim 5, wherein the detector is further configured to detect the characteristic point based on a change in the additional heart rate information with respect to an exercise tolerance of the individual.

8. The apparatus of claim 1, wherein the apparatus comprises a wearable device.

9. The apparatus of claim 1, wherein the heart rate information progressively increases during a first time period and sharply increases at the characteristic point.

10. The apparatus of claim 1, wherein the detector is further configured to differentiate the obtained heart rate information.

11. The apparatus of claim 10, wherein
    when the heart rate information is primarily differentiated, the characteristic point corresponds to a peak value, and
    when the heart rate information is secondarily differentiated, the characteristic point corresponds to zero.

12. The apparatus of claim 1, wherein the obtainer is further configured to accumulate heart rate information over a plurality of time periods,
    wherein heart rate information of a first time period of the plurality of time periods comprises an average of heart rate data obtained during the first time period, and
    wherein heart rate information of each subsequent time period of the plurality of time periods after the first time period comprises a moving average.

13. A method of determining an exercise capability of an individual, the method comprising:
    obtaining, by a user apparatus, heart rate information of the individual while the individual performs an exercise;
    detecting, by the user apparatus, a characteristic point from the obtained heart rate information,
    wherein the characteristic point corresponds to a point at which a gradient of the heart rate information changes;
    determining, by the user apparatus, an elapsed time until the characteristic point is detected;
    obtaining, by the user apparatus, determination information to be used to determine an exercise capability of the individual based on the characteristic point and the elapsed time; and
    providing, by the user apparatus, exercise guidance information based on the determined exercise capability.

14. The method of claim 13, further comprising:
    outputting information comprising at least one of a visual indicating information, an auditory indicating information, or a tactile indicating information to the individual using a preset scheme.

15. The method of claim 14, wherein the outputting further comprises suspending an output of at least one of the visual indicating information, the auditory indicating information, and the tactile indicating information when the characteristic point is detected.

16. The method of claim 13, wherein the determining of the exercise capability comprises obtaining additional heart rate information corresponding to anaerobic threshold information of the individual based on at least one of the characteristic point and physical information of the individual.

17. The method of claim 16, wherein the determining of the exercise capability further comprises determining the exercise capability based on the additional heart rate information corresponding to the anaerobic threshold information.

18. The method of claim 16, wherein the detecting further comprises detecting the characteristic point based on a change in the additional heart rate information with respect to an exercise tolerance of the individual.

19. The method of claim 13, wherein the characteristic point is detected using a predetermined scheme.

* * * * *